United States Patent
Guerin et al.

(10) Patent No.: US 7,833,290 B2
(45) Date of Patent: Nov. 16, 2010

(54) COMPOSITION COMPRISING A DERIVATIVE OF HERMATOXYLIN, OF HEMATEIN, OF BRAZILIN OR OF BRAZILEIN, METAL SALT, HYDROGEN PEROXIDE, AND (BI)CARBONATE AND HAIR DYEING METHOD THEREWITH

(75) Inventors: Frédéric Guerin, Paris (FR); Luc Gourlaouen, Asnieres (FR)

(73) Assignee: L'Oreal S. A., Paris (FR)

( * ) Notice: Subject to any disclaimer, the term of this patent is extended or adjusted under 35 U.S.C. 154(b) by 0 days.

(21) Appl. No.: 12/637,220

(22) Filed: Dec. 14, 2009

(65) Prior Publication Data
US 2010/0146718 A1 Jun. 17, 2010

Related U.S. Application Data

(60) Provisional application No. 61/140,305, filed on Dec. 23, 2008.

(30) Foreign Application Priority Data
Dec. 12, 2008 (FR) .................. 0858556

(51) Int. Cl.
*A61Q 5/10* (2006.01)
*C07D 311/00* (2006.01)

(52) U.S. Cl. .............. 8/405; 8/435; 8/452; 8/576; 8/594; 132/202; 132/208; 549/383

(58) Field of Classification Search .......... 8/405, 8/435, 452, 576, 594; 132/202, 208; 549/383
See application file for complete search history.

(56) References Cited

U.S. PATENT DOCUMENTS

| 4,801,302 | A * | 1/1989 | Grollier | ............ | 8/429 |
| 6,953,486 | B2 | 10/2005 | Pruche | | |
| 2003/0103917 | A1 | 6/2003 | Pruche | | |

FOREIGN PATENT DOCUMENTS

| DE | 199 59 480 A1 | 6/2001 |
| DE | 10 2005 062 830 A1 | 1/2007 |
| EP | 0 124 393 A1 | 11/1984 |
| EP | 0 664 114 A1 | 7/1995 |
| FR | 2 598 318 A1 | 11/1987 |
| FR | 2 814 945 A1 | 4/2001 |
| FR | 2 814 946 A1 | 4/2001 |
| FR | 2 814 947 A1 | 4/2001 |
| FR | 2 814 943 A1 | 4/2002 |
| JP | 08 012539 | 1/1996 |

OTHER PUBLICATIONS

STIC Search Report dated Jul. 13, 2010.*
French Search Report for FR 0858556, dated Aug. 27, 2009.
French Search Report for FR 0858554, dated Aug. 19, 2009.
French Search Report for FR 0858555, dated Aug. 27, 2009.
French Search Report for FR 0858557, dated Aug. 19, 2009.
French Search Report for FR 0858558, dated Aug. 24, 2009.
English language abstract of DE 199 59 480 A1, Jun. 21, 2001.
English language abstract of DE 10 2005 062 830 A1, Jan. 4, 2007.
English language abstract of EP 0 124 393 A1, Jul. 11, 1984.
English language abstract of FR 2 814 943 A1, Apr. 12, 2002.
English language abstract of FR 2 814 945 A1, Apr. 12, 2002.
English language abstract of JP 08 012539, Jan. 16, 1996.
Co-pending Application filed Dec. 14, 2009.
Co-pending Application filed Dec. 14, 2009.
Co-pending Application filed Dec. 14, 2009.
Co-pending Application filed Dec. 14, 2009.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The disclosure relates to methods for dyeing keratinous fibers by treatment of said fibers with i) at least one entity chosen from hematoxylin, hematein, brazilin, brazilein, and their derivatives, ii) at least one metal salt, iii) hydrogen peroxide or at least one system which generates hydrogen peroxide and iv) at least one (bi)carbonate. The disclosure also relates to multicompartment devices and compositions comprising the ingredients i), ii), iii) and iv).

21 Claims, No Drawings

COMPOSITION COMPRISING A DERIVATIVE OF HERMATOXYLIN, OF HEMATEIN, OF BRAZILIN OR OF BRAZILEIN, METAL SALT, HYDROGEN PEROXIDE, AND (BI)CARBONATE AND HAIR DYEING METHOD THEREWITH

This application claims benefit of U.S. Provisional Application No. 61/140,305, filed Dec. 23, 2008. This application also claims benefit of priority under 35 U.S.C. §119 to French Patent Application No. 0858556, filed Dec. 12, 2008.

The present disclosure relates to compositions, methods, and kits for dyeing keratinous fibers, such as compositions, methods, and kits making use of i) at least one entity chosen from hematoxylin, hematein, brazilin, brazilein, and/or derivatives thereof, ii) at least one metal salt, iii) at least hydrogen peroxide or at least one system which generates hydrogen peroxide and iv) at least one (bi)carbonate.

So-called "permanent" colorings can be obtained with dyeing compositions comprising oxidation dye precursors, generally known as oxidation bases, such as ortho- or para-phenylenediamines, ortho- or para-aminophenols and heterocyclic compounds. These oxidation bases can be colorless or weakly colored compounds which, in combination with oxidizing products, can give rise, by an oxidative coupling process, to colored compounds. The shades obtained can be varied by combining these oxidation bases with couplers or coloring modifiers, the latter being chosen, e.g., from aromatic meta-diamines, meta-aminophenols, meta-diphenols and certain heterocyclic compounds, such as indole compounds. This oxidation dyeing method can involve applying, to the keratinous fibers, bases or a mixture of bases and of couplers with hydrogen peroxide ($H_2O_2$ or aqueous hydrogen peroxide solution) as oxidizing agent, allowing diffusion to occur, and then rinsing the fibers. The colorings which result therefrom can be permanent, powerful and resistant to external agents, e.g., to light, bad weather, washing operations, perspiration and rubbing actions.

However, the commercial hair dyes which comprise them can exhibit disadvantages, such as staining or problems of smell, of comfort or of decomposition of the keratinous fibers. This can be the case, for example, with oxidation dyeing operations.

There exists a need to develop dyeing methods which make it possible to obtain powerful colorings using dyes or dye precursors, while limiting the decoloration of the keratinous fibers. There further exists a need to obtain colorings which are less aggressive to the hair and, at the same time, which can withstand external agents (light, bad weather, shampooing operations) and which can be persistent and homogeneous while remaining powerful and chromatic. The subject matter of the present disclosure, inter alia, can in some embodiments satisfy one or more of these needs.

An aspect of the present disclosure is a method for dyeing keratinous fibers, comprising treating said fibers with:

i) at least one entity chosen from compounds chosen from synthetic and natural compounds of formulae (I) and (II), their mesomeric forms, their stereoisomers, their addition salts with an acid or base that is cosmetically acceptable, and their hydrates:

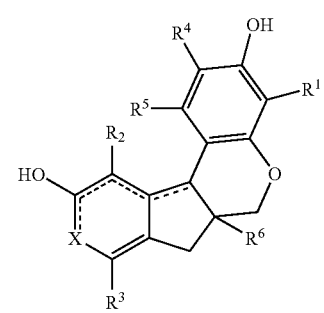

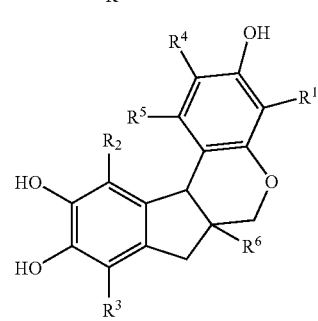

and wherein:

≡≡≡ represents a single or conjugated double carbon-carbon bond;

X represents either:

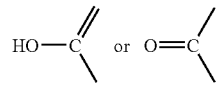

$R^1$, $R^2$, $R^3$, $R^4$, $R^5$ and $R^6$, which are identical or different, are chosen from a hydrogen atom, a hydroxy group, an optionally substituted alkyl group, optionally substituted alkoxy, and an optionally substituted acyloxy group;

ii) at least one metal salt, iii) hydrogen peroxide or at least one system which generates hydrogen peroxide, and iv) at least one (bi)carbonate.

Another aspect of the present disclosure is a cosmetic dyeing composition comprising:

i) at least one entity chosen from compounds chosen from synthetic and natural compounds of formulae (I) and (II), their mesomeric forms, their stereoisomers, their addition salts with an acid or base that is cosmetically acceptable, and their hydrates:

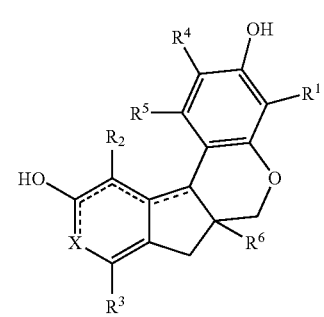

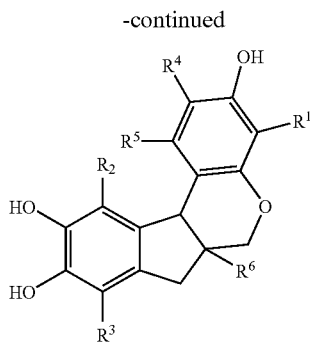

(II)

and wherein:

---- represents a single or conjugated double carbon-carbon bond;

X represents either:

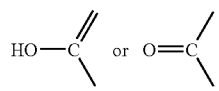

$R^1$, $R^2$, $R^3$, $R^4$, $R^5$ and $R^6$, which are identical or different, are chosen from a hydrogen atom, a hydroxy group, an optionally substituted alkyl group, optionally substituted alkoxy, and an optionally substituted acyloxy group;

ii) at least one metal salt, iii) hydrogen peroxide or at least one system which generates hydrogen peroxide, and iv) at least one (bi)carbonate.

Another aspect of the disclosure is a multicompartment device comprising from 2 to 5 compartments comprising from 2 to 5 compositions in which the ingredients i) at least one entity chosen from compounds chosen from synthetic and natural compounds of formulae (I) and (II), their mesomeric forms, their stereoisomers, their addition salts with an acid or base that is cosmetically acceptable, and their hydrates:

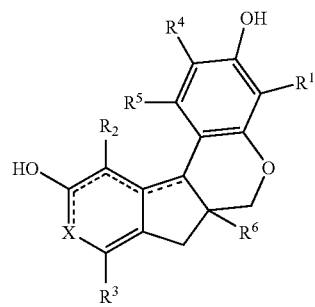

(I)

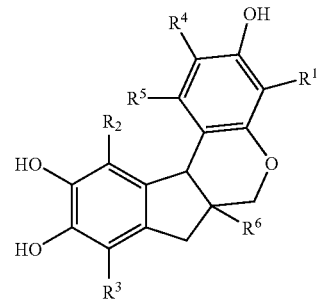

(II)

and wherein:

---- represents a single or conjugated double carbon-carbon bond;

X represents either:

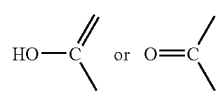

$R^1$, $R^2$, $R^3$, $R^4$, $R^5$ and $R^6$, which are identical or different, are chosen from a hydrogen atom, a hydroxy group, an optionally substituted alkyl group, optionally substituted alkoxy, and an optionally substituted acyloxy group;

ii) at least one metal salt, iii) hydrogen peroxide or at least one system which generates hydrogen peroxide, and iv) at least one (bi)carbonate, and optionally water, are distributed.

The methods according to the disclosure can exhibit the benefit of imparting to keratinous fibers, such as human keratinous fibers, powerful and chromatic colorings which can be resistant to washing operations, to perspiration, to sebum and to light and which can be in addition long lasting without a detrimental change to said fibers. Furthermore, the colorings obtained using the methods of the disclosure can give homogeneous colors from the root to the tip of a fiber (that is, they can have low dyeing selectivity).

i) The Compounds of Formulae (I) and (II);

The methods, compositions, and kits of the disclosure involve at least one entity chosen from synthetic or natural compounds of formulae (I) and (II), their mesomeric forms, their stereoisomers, their addition salts with an acid or base that is cosmetically acceptable, and their hydrates. The compounds of formula (I) as defined above may be in two mesomeric forms denoted by (Ia) and (Ib):

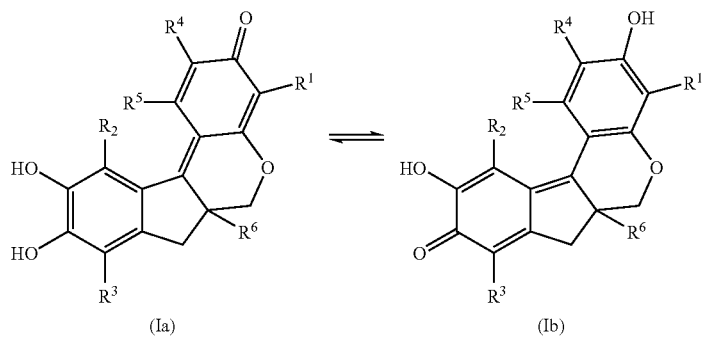

(Ia)          (Ib)

$R^1$, $R^2$, $R^3$, $R^4$, $R^5$ and $R^6$, which can be identical or different, can be chosen from a hydrogen atom, a hydroxy radical, optionally substituted alkyl radicals, optionally substituted alkoxy radicals, and optionally substituted acyloxy radicals.

The alkyl radicals can be saturated and linear or branched hydrocarbon radicals, for example, $C_1$-$C_{20}$ radicals, $C_1$-$C_{10}$ radicals, $C_1$-$C_6$ alkyl radicals, such as methyl, ethyl, propyl, butyl, pentyl and hexyl.

The alkoxy radicals can be alkyloxy radicals with the alkyl as defined above, e.g., $C_1$-$C_{10}$ alkoxy radicals, such as methoxy, ethoxy, propoxy and butoxy.

The alkoxyalkyl radicals can be $(C_1$-$C_{20})$alkoxy$(C_1$-$C_{20})$ alkyl radicals, such as methoxymethyl, ethoxymethyl, methoxyethyl, ethoxyethyl, etc.

The alkyl or alkoxy radicals, when they are optionally substituted, may be substituted by at least one substituent carried by at least one carbon atom, and the substituent can be chosen from:
   a halogen atom;
   a hydroxyl group;
   a $C_1$-$C_2$ alkoxy radical;
   a $C_1$-$C_{10}$ alkoxycarbonyl radical;
   a (poly)hydroxy$(C_2$-$C_4)$alkoxy radical;
   an amino radical;
   a 5- or 6-membered heterocycloalkyl radical;
   an optionally cationic 5- or 6-membered heteroaryl radical, such as an imidazolium radical, which is optionally substituted by a $(C_1$-$C_4)$alkyl radical, for example, a methyl radical;
   an amino radical substituted by one or two identical or different $C_1$-$C_6$ alkyl radicals optionally carrying at least:
      one hydroxyl group,
      one amino group optionally substituted by one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other heteroatom other than or the same as nitrogen,
      one quaternary ammonium group —N$^+$R'R''R'''M$^-$ for which R', R'' and R''', which can be identical or different, represent a hydrogen atom or a $C_1$-$C_4$ alkyl group and M$^-$ represents the counterion of the corresponding organic acid, inorganic acid or halide,
   or one optionally cationic 5- or 6-membered heteroaryl radical, such as an imidazolium radical, optionally substituted by a $(C_1$-$C_4)$alkyl radical, for example, a methyl radical;
   an acylamino (—NR—COR') radical in which the R radical is a hydrogen atom or a $C_1$-$C_4$ alkyl radical optionally carrying at least one hydroxyl group and the R' radical is a $C_1$-$C_2$ alkyl radical; a carbamoyl $((R)_2$N—CO—) radical in which the R radicals, which can be identical or different, represent a hydrogen atom or a $C_1$-$C_4$ alkyl radical optionally carrying at least one hydroxyl group; an alkylsulfonylamino (R'SO$_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl $((R)_2$N—SO$_2$—) radical in which the R radicals, which can be identical or different, represent a hydrogen atom or a $C_1$-$C_4$ alkyl radical optionally carrying at least one hydroxyl group,
   a carboxyl radical in the acid form or salified form (e.g., salified with an alkali metal or a substituted or unsubstituted ammonium);
   a cyano group;
   a nitro group;
   a carboxyl or glycosylcarbonyl group;
   a phenylcarbonyloxy group optionally substituted by at least one hydroxyl group;
   a glycosyloxy group; and
   a phenyl group optionally substituted by at least one hydroxyl group.

Glycosyl radical is understood to mean a radical resulting from a mono- or polysaccharide.

The compounds of formula (I) used in the methods of the disclosure can be natural or synthetic. The natural compounds include the compounds which are present in nature and which may be reproduced by chemical synthesis.

The salts of the compounds of formula (I) of the disclosure can be salts of acids or of bases that are cosmetically acceptable. The acids can be inorganic or organic acids.

In some embodiments, the acid is hydrochloric acid, which results in the chlorides.

The bases can be inorganic or organic bases. For example, the bases can be alkali metal hydroxides, such as sodium hydroxide, which results in sodium salts.

In some embodiments, the compounds of formula (I) or (II) comprise a radical $R^6$ which represents a hydroxyl group.

In some embodiments, the compounds of formula (I) or (II) comprise an $R^1$ chosen from a hydrogen atom and a hydroxyl group.

In some embodiments, the compounds of formula (I) or (II) are chosen from the compounds of formula (I).

In some embodiments, the methods of dyeing keratinous fibers use, as ingredient i), at least one compound chosen from the natural compounds of hematoxylin, hematein, brazilin and brazilein.

Among the compounds of hematoxylin/hematein and of brazilin/brazilein, mention may be made, by way of example, of hematoxylin (Natural Black 1) and brazilin (Natural Red 24), compounds from the family of indo-chromanes, which can be acquired commercially. The latter may exist in an oxidized form and be obtained by synthetic routes or routes for extraction from plants or vegetables known for being rich in these compounds.

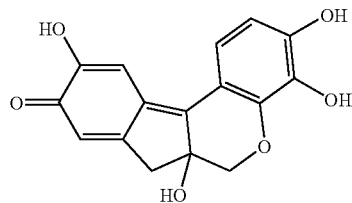

Hematein (oxidized from)
belonging to the formula (I)

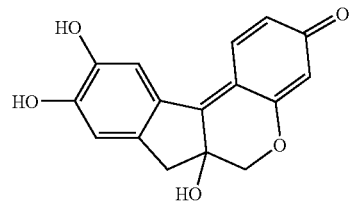

Brazilein (oxidized form) belonging
to the formula (I)

-continued

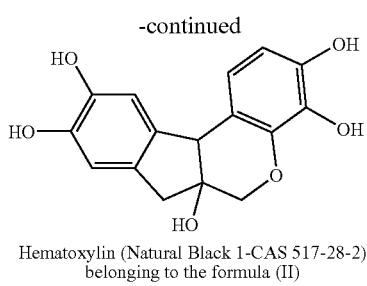

Hematoxylin (Natural Black 1-CAS 517-28-2)
belonging to the formula (II)

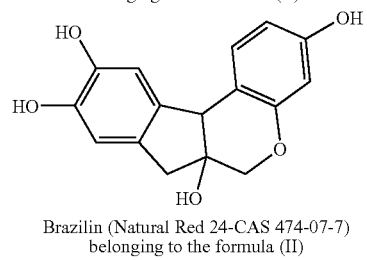

Brazilin (Natural Red 24-CAS 474-07-7)
belonging to the formula (II)

The at least one entity may be provided and/or used in the form of extracts. Use may be made, for example, of extracts of any of the following plants (genus and species): *Haematoxylon campechianum, Haematoxylon brasiletto, Caesalpinia echinata, Caesalpinia sappan, Caesalpinia spinosa*, and *Caesalpina brasiliensis*.

The extracts can be obtained by extraction of various parts of plants such as, for example, the root, wood, bark or leaf.

According to some embodiments, natural hematoxylin/hematein and/or brazilin/brazilein are derived from the wood of logwood or brazilwood trees.

In some embodiments, the at least one entity is a natural compound of compounds of formula (I) or (II) of the disclosure that can be derived from plant extracts.

In some embodiments, the at least one entity represents at least 80% by weight relative to the total weight of the ingredients i), ii), iii) and iv) or i), ii) and iii) as defined above. The weight of the at least one entity can be determined either as the weight of the at least one extract in which it is provided or as the weight of the at least one active material.

It is also possible to use mixtures of vegetable extracts.

The natural extracts according to the disclosure may be in the form of powders or liquids. In some embodiments, the extracts of the disclosure can be in the form of powders.

According to the disclosure, the synthetic or natural compound or compounds of formula (I) and (II) such as the hematoxylin/hematein and brazilin/brazilein compounds and/or the natural extract(s) used as ingredient i) in at least one composition of use in the method according to the disclosure can range from 0.001% to 20% by weight of the total weight of the composition(s) containing the compound or compounds of formula (I) and (II) such as the hematoxylin/hematein and brazilin/brazilein compounds or the extract or extracts.

As regards the pure compounds of formula (I) and (II) such as the pure hematoxylin/hematein and brazilin/brazilein compounds, the content in the composition or compositions containing them can range, for example, from 0.001% to 5% by weight of each of these compositions.

As regards the extracts, the content in the composition or compositions containing the extracts as is can range, for example, from 0.5% to 20% by weight of each of these compositions.

ii) Metal Salt

The methods of the disclosure use at least one ingredient ii) which is a metal salt.

In some embodiments, the metal salt is a salt of a divalent metal. In some embodiments, the metal salt is a salt of a transition metal. In some embodiments, the metal salt is not a salt of an alkali metal.

In some embodiments, the at least one metal salt is chosen from manganese (Mn) and zinc (Zn) salts.

Within the meaning of the present disclosure, "salt" is understood to include the oxides and hydroxides of these metals and the salts proper that can result from the action of an acid on a metal. In some embodiments, the at least one salt is not an oxide. In some embodiments, the at least one salt is not a hydroxide. Mention may be made, among the salts, of halides, such as chlorides, fluorides and iodides, sulfates, phosphates, nitrates, perchlorates and salts of carboxylic acids and polymeric complexes which can support said salts, and also their mixtures.

In some embodiments, the manganese salt is other than manganese carbonate, manganese hydrogencarbonate or manganese dihydrogencarbonate.

The salts of carboxylic acids which can be used in the disclosure also include salts of hydroxylated carboxylic acids, such as gluconate.

Mention may be made, as examples of polymeric salts, of manganese pyrrolidonecarboxylate.

Mention may be made, as examples, of manganese chloride, manganese fluoride, manganese acetate tetrahydrate, manganese lactate trihydrate, manganese phosphate, manganese iodide, manganese nitrate trihydrate, manganese bromide, manganese perchlorate tetrahydrate, manganese sulfate monohydrate and manganese gluconate. In some embodiments, the at least one salt is chosen from manganese gluconate and manganese chloride. In some embodiments, the at least one salt comprises manganese gluconate and manganese chloride.

Mention may be made, among zinc salts, of zinc sulfate, zinc gluconate, zinc chloride, zinc lactate, zinc acetate, zinc glycinate and zinc aspartate.

The manganese and zinc salts can be introduced in the solid form into the compositions or else can originate from a natural, mineral or thermal, water rich in these ions or also from sea water (for example, Dead Sea water). They can also originate from inorganic compounds, such as earths or ocres, such as clays (for example green clay), or from plant extracts comprising.

For example, the metal salts of the disclosure can have oxidation states of 2, such as Mn(II) and Zn(II).

In some embodiments, the metal salt or salts used can be present in an amount ranging from 0.001% to 0.1% by weight of the total weight of the composition(s) comprising this or these metal salts, for example, from 0.05% to 10% by weight.

iii) Hydrogen Peroxide or a System which Generates Hydrogen Peroxide

In the context of the present disclosure, the third constituent is iii) hydrogen peroxide or a system which generates hydrogen peroxide, such as:

a) urea hydrogen peroxide;

b) at least one polymeric complex which releases hydrogen peroxide, such as polyvinylpyrrolidone/$H_2O_2$, or other polymeric complexes such as those described in U.S. Pat. Nos. 5,008,093, 3,376,110, and 5,183,901 (in some embodiments, the at least one polymeric complex which releases hydrogen peroxide can be provided in the form of a powder);

c) at least one oxidase which produces hydrogen peroxide in the presence of an appropriate substrate (for example, glucose in the case of glucose oxidase or uric acid with uricase);

d) at least one metal peroxide which, in water, generates hydrogen peroxide, such as calcium peroxide or magnesium peroxide;

e) at least one perborate; or f) at least one percarbonate.

In some embodiments, the composition or compositions comprise at least one system which generates hydrogen peroxide, chosen from a) urea hydrogen peroxide; b) at least one polymeric complex which releases hydrogen peroxide, such as polyvinylpyrrolidone/$H_2O_2$; c) at least one oxidase; d) at least one perborate; and e) at least one percarbonate.

In some embodiments, the third constituent is hydrogen peroxide or urea peroxide, for example, hydrogen peroxide.

Furthermore, the composition or compositions comprising the hydrogen peroxide or the least one system which generates hydrogen peroxide can also include one or more of various adjuvants used conventionally in compositions for dyeing the hair, which include those described herein.

In some embodiments, the hydrogen peroxide or the at least one system which generates hydrogen peroxide can be present in an amount ranging from 0.001% to 12% by weight of hydrogen peroxide, with respect to the total weight of the composition or compositions comprising it or them, and more for example, from 0.2% to 2.7% by weight.

In some embodiments, the at least one system which generates hydrogen peroxide does not comprise material that is effervescent as a solid. Materials that are effervescent as a solid include powders and pebbles that can produce bubbling, foaming or liberation of a gas, which can occur, for example, upon contact with a solvent or solution, such as a protic solvent, a solution at acidic pH, or a solution or solvent comprising a free Lewis acid.

iv) (Bi)carbonate

In the context of the present disclosure, the fourth ingredient can be chosen from carbonates and bicarbonates.

Carbonates and bicarbonates (collectively, (bi)carbonates) include:

a) carbonates of alkali metals ($Met^+_2CO_3^{2-}$), of alkaline earth metals ($Met'^{2+}CO_3^{2-}$), of ammonium ($(R''_4N^+)_2CO_3^{2-}$) or of phosphonium ($(R''_4P^+)_2CO_3^{2-}$), with Met' representing an alkaline earth metal and Met representing an alkali metal and R", which can be identical or different, representing a hydrogen atom or an optionally substituted ($C_1$-$C_6$)alkyl group, such as a hydroxyethyl group, and b) bicarbonates, also known as hydrogencarbonates, with the following formulae:

$R'^+HCO_3^-$, with R' representing a hydrogen atom, an alkali metal or an ammonium $R''_4N^+$ or phosphonium $R''_4P^+$ group, where R", which can be identical or different, represent a hydrogen atom or an optionally substituted ($C_1$-$C_6$)alkyl group, such as a hydroxyethyl group, and, when R' represents a hydrogen atom, the hydrogencarbonate is then referred to as dihydrogencarbonate ($CO_2$, $H_2O$); and $Met'^{2+}(HCO_3^-)_2$, with Met' representing an alkaline earth metal.

In some embodiments, the fourth ingredient is chosen from alkali metal or alkaline earth metal (bi)carbonates, such as alkali metal (bi)carbonates.

Mention may be made of sodium, potassium, magnesium or calcium carbonates or hydrogencarbonates and their mixtures, such as sodium hydrogencarbonate. These hydrogencarbonates can originate from a natural water, for example spring water from the Vichy basin or from La Roche-Posay or Badoit water. In some embodiments, the at least one (bi) carbonate is chosen from sodium carbonate [497-19-8]=$Na_2CO_3$, sodium hydrogencarbonate or sodium bicarbonate [144-55-8]=$NaHCO_3$, and calcium bicarbonate (also known as calcium dihydrogencarbonate)=$Ca(HCO_3)_2$.

According to the disclosure, the (bi)carbonate agent or agents used can be present in an amount ranging from 0.001% to 10% by weight of the total weight of the composition or compositions comprising the (bi)carbonate agent or agents, for example, from 0.005% to 5% by weight.

v) Water

In some embodiments, water is used in the method of the disclosure. It can be provided by wetting of the keratinous fibers and/or as part of the composition or compositions comprising the compounds i) to iv) as defined above, and/or from at least one other composition.

In some embodiments, the water originates at least from a composition comprising at least one compound chosen from i) to iv) as defined above.

In some embodiments, at least one of the at least one synthetic or natural compound (chosen from compounds of formulae (I) and (II) and their mesomeric forms, their stereoisomers, their addition salts with an acid or base that is cosmetically acceptable, and their hydrates), the at least one metal salt, the hydrogen peroxide or at least one system which generates hydrogen peroxide, or the at least one (bi)carbonate is applied to keratinous fibers in a composition comprising water in an amount greater than or equal to 50%, 60%, 70%, 80%, 90%, 91%, 92%, 93%, 94%, 95%, 96%, 97%, or 98% by weight of the total weight of the composition. In some embodiments, at least one of the at least one entity chosen from synthetic and natural compounds chosen from compounds of formulae (I) and (II) and their mesomeric forms, their stereoisomers, their addition salts with an acid or base that is cosmetically acceptable, and their hydrates, the at least one metal salt, the hydrogen peroxide or at least one system which generates hydrogen peroxide, or the at least one (bi) carbonate is applied to keratinous fibers in a composition comprising water in an amount ranging from 50% to 98%; from 60% to 97%; from 70% to 96%; from 80% to 95%; from 90% to 95%; from 60% to 97%; from 70% to 96%; from 80% to 95%; or from 90% to 95%.

In some embodiments, the cosmetic compositions according to the disclosure comprise at least one synthetic or natural compound chosen from compounds of formulae (I) and (II) and their mesomeric forms, their stereoisomers, their addition salts with an acid or base that is cosmetically acceptable, and their hydrates; at least one metal salt; hydrogen peroxide or at least one system which generates hydrogen peroxide; at least one (bi)carbonate, and water, wherein the water is present in an amount greater than or equal to 50%, 60%, 70%, 80%, 90%, 91%, 92%, 93%, 94%, 95%, 96%, 97%, or 98% by weight of the total weight of the cosmetic composition.

In some embodiments, the cosmetic compositions according to the disclosure comprise at least one synthetic or natural compound chosen from compounds of formulae (I) and (II) and their mesomeric forms, their stereoisomers, their addition salts with an acid or base that is cosmetically acceptable, and their hydrates; at least one metal salt; hydrogen peroxide or at least one system which generates hydrogen peroxide; at least one (bi)carbonate, and water, wherein the water is present in an amount ranging from 50% to 98%; from 60% to 97%; from 70% to 96%; from 80% to 95%; from 90% to 95%; from 60% to 97%; from 70% to 96%; from 80% to 95%; or from 90% to 95%.

In some embodiments, the multicompartment devices according to the disclosure comprise from 2 to 5 compartments comprising from 2 to 5 compositions which collectively comprise at least one synthetic or natural compound chosen from compounds of formulae (I) and (II) and their mesomeric forms, their stereoisomers, their addition salts with an acid or base that is cosmetically acceptable, and their hydrates; at least one metal salt; hydrogen peroxide or at least one system which generates hydrogen peroxide; at least one (bi)carbonate; and water, said 2 to 5 compositions being aqueous or pulverulent, with at least one of these compositions being aqueous, wherein water is present in the 2 to 5 compositions in a total amount greater than or equal to 50%, 60%, 70%, 80%, 90%, 91%, 92%, 93%, 94%, 95%, 96%, 97%, or 98% by weight of the total weight of the 2 to 5 compositions.

In some embodiments, the multicompartment devices according to the disclosure comprise from 2 to 5 compartments comprising from 2 to 5 compositions which collectively comprise at least one synthetic or natural compound chosen from compounds of formulae (I) and (II) and their mesomeric forms, their stereoisomers, their addition salts with an acid or base that is cosmetically acceptable, and their hydrates; at least one metal salt; hydrogen peroxide or at least one system which generates hydrogen peroxide; at least one (bi)carbonate; and water, said 2 to 5 compositions being aqueous or pulverulent, with at least one of these compositions being aqueous, wherein water is present in the 2 to 5 compositions in a total amount ranging from 50% to 98%; from 60% to 97%; from 70% to 96%; from 80% to 95%; from 90% to 95%; from 60% to 97%; from 70% to 96%; from 80% to 95%; or from 90% to 95%. In at least one embodiment, said 2 to 5 compositions can be aqueous or pulverulent, with at least one of these compositions being aqueous, wherein water is present in the 2 to 5 compositions in a total amount greater than or equal to 50% by weight of the total weight of the 2 to 5 compositions.

vi) Cosmetic Compositions

In some embodiments, the disclosure relates to a cosmetic dyeing composition comprising:

i) at least one entity chosen from synthetic and natural derivatives, alone or as mixtures, chosen from the derivatives of formulae (I) and (II) or their mesomeric forms, their stereoisomers, their addition salts with an acid or base that is cosmetically acceptable, and also the hydrates;

ii) at least one metal salt;

iii) hydrogen peroxide or at least one system which generates hydrogen peroxide; and iv) at least one (bi)carbonate or at least one system which generates (bi)carbonate(s).

In some embodiments, the cosmetic compositions according to the disclosure comprise a cosmetically acceptable coloring vehicle which comprises water, a mixture of water and of at least one organic solvent, or a mixture of organic solvents. In other embodiments, at least one of the cosmetic compositions according to the disclosure can be provided as a powder. Thus, they can be in pulverulent or non-pulverulent forms.

These compositions can comprise a coloring vehicle which generally comprises water or a mixture of water and of one or more organic solvents or a mixture of organic solvents.

The term "organic solvent" is understood to mean an organic substance capable of dissolving or dispersing another substance without modifying it chemically.

In some embodiments, the cosmetic dyeing compositions according to the disclosure comprise water.

In some embodiments, the cosmetic compositions according to the disclosure comprise i) **at least one entity chosen from compounds chosen from synthetic and natural compounds of formulae (I) and (II), ii) at least one metal salt, iii) hydrogen peroxide or at least one system which generates hydrogen peroxide, and iv) at least one (bi)carbonate, wherein the ingredients i) through iv) are mutually different, i.e., one entity or chemical species does not serve as two of the ingredients i) through iv).

The Organic Solvents:

Mention may be made, as organic solvents, for example, of lower $C_1$-$C_4$ alkanols, such as ethanol and isopropanol, polyols and polyol ethers, such as 2-butoxyethanol, propylene glycol, propylene glycol monomethyl ether, diethylene glycol monoethyl ether, diethylene glycol monomethyl ether or hexylene glycol, and aromatic alcohols, such as benzyl alcohol or phenoxyethanol.

The organic solvent(s) can be present in an amount ranging from 1% to 40% by weight, with respect to the total weight of the dyeing composition, or from 5% to 30% by weight.

The Adjuvants:

The composition or compositions of the coloring method in accordance with the disclosure can also include various adjuvants conventionally used in compositions for dyeing the hair, which can be chosen from anionic, cationic, nonionic, amphoteric or zwitterionic surface-active agents or their mixtures, anionic, cationic, nonionic, amphoteric or zwitterionic polymers or their blends, inorganic or organic thickening agents, such as anionic, cationic, nonionic and amphoteric polymeric associative thickeners, antioxidants, penetration agents, sequestering agents, fragrances, buffers, dispersing agents, conditioning agents, such as, for example, volatile or nonvolatile and modified or unmodified silicones, film-forming agents, ceramides, preservatives and opacifying agents.

Said adjuvants can be chosen from surface-active agents, such as anionic or nonionic surfactants or their mixtures, and inorganic or organic thickening agents.

The above adjuvant or adjuvants can be present in an amount, for each of them, ranging from 0.01% to 40% by weight, with respect to the weight of the composition, for example, from 0.1% to 20% by weight, with respect to the weight of the composition.

Of course, a person skilled in the art will take care to choose the optional additional compound or compounds so that the beneficial properties of the at least one composition of use in the coloring method in accordance with the disclosure are not, or not substantially, detrimentally affected by the envisaged addition or additions.

The Additional Dyes:

The dye composition comprising the ingredients i) to iv) as defined above and the method employing the ingredients i) to iv) as defined above can also comprise or also employ at least one direct dye.

These direct dyes can be, for example, chosen from those conventionally used in direct dyeing, among which may be mentioned any of the aromatic and/or nonaromatic dyes commonly used, such as neutral, acid or cationic nitrobenzene direct dyes, neutral, acid or cationic azo direct dyes, natural direct dyes other than ortho-diphenols, neutral, acid or cationic quinones such as anthraquinone direct dyes, azine, triarylmethane or indoamine direct dyes, methines, styryls, porphyrins, metalloporphyrins, phthalocyanines, methinecyanines and fluorescent dyes.

Mention may be made, among natural direct dyes, of lawsone, juglone, indigo, isatin, curcumin, spinulosin, apigenidine or orceins. Use may also be made of extracts or decoctions comprising these natural dyes such as cataplasms or henna-based extracts.

The direct dye or dyes then in the composition or compositions of the coloring method according to the disclosure, or of the composition according to the disclosure, can be present in an amount ranging from 0.001% to 10% by weight of the total weight of the composition or compositions employed, for example, from 0.05% to 5% by weight.

The cosmetic composition or compositions comprising the ingredients i) to iv) as defined above can also comprise at least one oxidation base and/or at least one coupler conventionally used for the dyeing of keratinous fibers.

Mention may be made, among the oxidation bases, of para-phenylenediamines, bisphenylalkylenediamines, para-aminophenols, bis-para-aminophenols, ortho-aminophenols, heterocyclic bases and their addition salts.

Mention may be made, among these couplers, of meta-phenylenediamines, meta-aminophenols, meta-diphenols, naphthalene couplers, heterocyclic couplers and their addition salts.

The oxidation base or bases present in the composition or compositions can be present each in an amount ranging from 0.001% to 10% by weight of the total weight of the dye composition or compositions.

The cosmetic composition(s) of the disclosure can be provided in various formulation forms, such as a powder, a lotion, a foam, a cream or a gel, or in any other form appropriate for carrying out dyeing of keratinous fibers. It can also be packaged as a propellant-free pump-action spray or under pressure in an aerosol container in the presence of a propellant and form a foam.

pH of the Composition(s)

In some embodiments, the pH of the aqueous composition or compositions comprising iv) the (bi)carbonate or (bi)carbonates is greater than 7; in some embodiments, said pH ranges from 8 to 12, e.g., from 8 to 10.

The pH of the composition or compositions comprising the hydrogen peroxide or a system which generates hydrogen peroxide can in some embodiments have a pH less than 7, e.g., a pH ranging from 1 to 5, such as if the composition or compositions do(es) not comprise (bi)carbonates.

In some embodiments, the composition or compositions comprising i) the compound or compounds of formula (I) or (II) of the disclosure and not comprising (bi)carbonates can be at a pH of less than 7, e.g., a pH ranging from 3 to 6.5.

According to a form of the disclosure, the compositions comprising ii) the metal salt or salts and not comprising (bi)carbonates can be at a pH of less than 7, e.g., a pH ranging from 3 to 6.5.

The pH of these compositions can be adjusted to the desired value using an acidifying or basifying agent or agents commonly used in the dyeing of keratinous fibers and/or using a conventional buffer system or systems.

Mention may be made, among the acidifying agents of the compositions used in the disclosure, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

In some embodiments, a basifying agent is added to at least one of the compositions of the coloring method comprising the (bi)carbonate or (bi)carbonates. This basic agent can be chosen from aqueous ammonia, alkali metal carbonates, alkanolamines, such as mono-, di- and triethanolamines, and their derivatives, sodium or potassium hydroxides and the compounds of formula (IV):

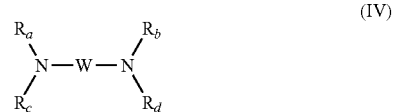

in which formula (IV) W is a propylene residue optionally substituted by a hydroxyl group or a $C_1$-$C_4$ alkyl radical and $R_a$, $R_b$, $R_c$ and $R_d$, which can be identical or different, represent a hydrogen atom, a $C_1$-$C_4$ alkyl radical or a $C_1$-$C_4$ hydroxyalkyl radical.

vii) Single- or Multistage Coloring Method

In some embodiments, the coloring method is carried out in at least one stage, by application to the keratinous fibers of at least one cosmetic composition comprising, together or separately, in said at least one composition, the following ingredients:

i) at least one synthetic or natural entity chosen from the compounds of formulae (I) and (II) and their mesomeric forms, their stereoisomers, their addition salts with an acid or base that is cosmetically acceptable, and their hydrates;

ii) at least one metal salt, such as the salts of Mn and Zn;

iii) hydrogen peroxide or at least one system which generates hydrogen peroxide; and iv) at least one (bi)carbonate.

This is to say, according to the disclosure, the above ingredients i)-iv) can be added in one stage or in multiple stages. They can be added in the form of one composition that comprises each of ingredients i)-iv), or they can be added in the form of at least two compositions that collectively comprise each of ingredients i)-iv).

In some embodiments, at least one composition comprising at least one of the ingredients i) to iv) is aqueous.

In some embodiments, there is a leave-in time between the stages of application of the compositions comprising the ingredient or ingredients i), ii), iii) and/or iv). In some embodiments, the leave-in time ranges from 3 to 120 minutes, such as from 10 to 60 minutes or from 15 to 45 minutes.

In the methods of the disclosure, the compound or compounds iv) can be:

either in a mixture with at least one of the ingredients i), ii) and iii), thus being applied at the same time as at least one of these ingredients;

or applied separately after application of at least one cosmetic composition comprising at least one of the ingredients i), ii) and iii), such as a composition comprising the ingredients i), ii) and iii); or else can be applied together with the ingredient iii) after application of a cosmetic composition comprising the ingredients i) and ii).

In some embodiments, the coloring methods comprise one or two stages of application of the above ingredients.

In some embodiments, the methods for coloring keratinous fibers can be carried out in a single stage by the application, to the keratinous fibers, of a cosmetic dye composition comprising i), ii), iii) and iv) as defined above.

In some embodiments, there is a leave-in time ranging from 3 to 120 minutes, such as from 10 to 60 minutes or from 15 to 45 minutes.

In some embodiments, the method for coloring keratinous fibers is carried out in two stages.

In some embodiments of the two-stage method, the first stage comprises applying, to said fibers, a first cosmetic composition comprising the ingredients i), ii) and iii) as defined above and then, a second stage comprises applying a cosmetic composition comprising the ingredient iv) as defined above to said fibers, it being understood that at least one of the two compositions is aqueous. In some embodiments, one of the two compositions is aqueous and the other is not.

In other embodiments of the two-stage method, the first stage comprises applying, to said fibers, a first composition comprising the ingredients i) and ii) as defined above and then, a second stage comprises applying a second cosmetic composition comprising the ingredients iii) and iv) as defined above to said fibers.

In some embodiments, the method for coloring keratinous fibers is carried out in at least two stages ending by a treatment of the keratin fibers with the ingredient iv) and can be followed by a post-treatment stage or stages such as a shampooing stage with the aid of classic shampooing, a rinse stage such as with water and/or a keratin fibers dry stage by a heat treatment such as defined hereinafter; provided that said process does not comprise an intermediate rinse stage just before the step applies ingredient iv) to the keratin fibers.

In some embodiments, the method for coloring keratinous fibers is carried out in two stages: in the first stage, the ingredients i) and ii) are together applied to the keratin fibers, and then in a second stage the ingredients iii) and iv) can be applied to the keratinous fibers. In some embodiments, in the first stage the ingredients i), ii) and iii) are together applied to the keratinous fibers, then in a second stage the ingredient iv) is applied to the keratinous fibers. These processes can be followed by a post-treatment comprising at least one stage, such as a rinse stage, e.g., with water and/or a shampooing stage with the aid of classic shampooing, and/or a keratinous fibers dry stage by heat treatment such as defined hereinafter.

In some embodiments, the method for coloring keratinous fibers in at least 2 stages is not carried out with an intermediate rinse stage between the first and second stages, i.e., between the treatment of keratinous fibers with the mixture of ingredients i), ii), iii) and the treatment of keratinous fibers with the ingredient iv), or between the treatment of keratinous fibers with the mixture of ingredients i), ii) and the treatment of keratinous fibers with the mixture of iii) and iv).

In some embodiments, keratinous fibers, just before the step which carries out ingredient iv), can be at least one of:
a) mechanically wiped such as defined herein;
b) dried by heating treatment such as defined herein;
c) unrinsed i.e. stages can be successively carried out.

For example, in some embodiments between the first and second stages of said method keratinous fibers can be at least one of:
a) mechanically wiped such as described herein after;
b) dried by heating treatment such as described herein after;
c) unrinsed i.e. stages can be successively carried out.

For instance, between the first and second stages the keratinous fibers can be wiped via the absorbent item, such as a piece of cloth, such as a towel, a terry towel, or a dish towel, or absorbent paper, such as kitchen towels, or the keratinous fibers can be dried by heating with heat treatment at a temperature ranging from 60 to 220° C. and such as from 120 and 200° C.

According to another embodiment of the method for coloring keratinous fibers in at least 2 stages, it is carried out with an intermediate very fast rinse stage between the first and second stages i.e. between the treatment of keratinous fibers with the mixture of ingredients i), ii), iii) and iv) or between the treatment of keratinous fibers with the mixture of ingredients i), ii) and the mixture of iii), iv). The period of rinse stage length ranges from 1 second to 1 minute, such as from 1 second and 30 seconds, and for instance ranging from 2 and 5 seconds such as 2 seconds, under tap water or tap shower water with a strong water jet. The latter fast rinsed stage is followed by a mechanical wiping such as defined herein after.

For these latter methods, the leave-in time after application of the cosmetic composition for the first stage can range from 3 to 120 minutes, such as from 10 to 60 minutes or from 15 to 45 minutes. The leave-in time after application of the second cosmetic composition for the second stage can range from 3 to 120 minutes, such as from 3 to 60 minutes or from 5 to 30 minutes.

Whatever the method of application, the application temperature generally ranges from ambient temperature (15 to 25° C.) to 80° C., such as from 15 to 45° C. Thus, it is possible, after application of the composition according to the disclosure, to subject the hair to a heat treatment by heating at a temperature ranging from 30 to 60° C. In practice, this operation can be carried out using a hair styling hood, a hair dryer, a dispenser of infrared rays and other conventional heating devices.

Use may be made, both as device for heating and for smoothing the hair, of a heating iron at a temperature ranging from 60 to 220° C., such as from 120 to 200° C.

A form of the disclosure relates to a coloring method which is carried out at ambient temperature (25° C.).

In all the forms and in all the alternative forms of the methods described above, the compositions mentioned can be ready-for-use compositions which can result from the mixing, at the time of use, of two or more compositions and of compositions present in dyeing kits.

viii) Stage(s) of Mechanical Wiping and/or of Drying:

The methods for dyeing keratinous fibers according to the disclosure comprise at least one intermediate stage of mechanical wiping of the fibers and/or of drying.

The mechanical wiping and drying stages are also called "controlled leave-in" stages, which differ from a "rinse-out" stage performed under an intense water jet, and from a "non rinsing" or "leave in" procedure, in which there is immediate progression from the first to the second stage of development.

Mechanical wiping of the fibers is understood to mean the rubbing of an absorbent item over the fibers and the physical withdrawal, via the absorbent item, of the surplus of ingredient(s) which has/have not penetrated into the fibers. The absorbent item can be a piece of cloth, such as a towel, e.g., a terry towel, a dish towel, or paper towel or other absorbent paper.

According to some embodiments of the disclosure for the method for coloring keratinous fibers, the mechanical wiping is made and let said fibers wets without a total drying of keratinous fibers.

Drying is understood to mean the action of evaporating the organic solvents and/or water occurring in one or more compositions used in the methods of the disclosure, comprising or not comprising one or more ingredients i) to iv) as defined above. Drying can be carried out via a heat source (convection, conduction or radiation) by sending, for example, a hot gas stream, such as air, which promotes the evaporation of the solvent or solvents. Mention may be made, as heat source, of a hair dryer, including hood hair dryers, an iron for smoothing the hair, a dispenser of infrared rays, and any other conventional heating device.

ix) Dyeing Device or "Kit"

Another aspect of the disclosure is a dyeing "kit" or multicompartment device. This kit can comprise from 2 to 5 compartments comprising from 2 to 5 compositions in which the following ingredients can be distributed:

i) at least one entity chosen from compounds chosen from synthetic and natural compounds of formulae (I) and (II), their mesomeric forms, their stereoisomers, their addition salts with an acid or base that is cosmetically acceptable, and their hydrates;

ii) at least one metal salt;

iii) hydrogen peroxide or at least one system which generates hydrogen peroxide; and iv) at least one (bi)carbonate, said compositions being aqueous or pulverulent. In some embodiments, at least one of these compositions is aqueous.

In some embodiments, the kit comprises five compartments, the first four compartments respectively comprising the ingredients, as powders, i), ii), iii) and iv) as defined above and the fifth compartment containing an aqueous composition, such as water. In this case, the compound or compounds iii) are hydrogen peroxide precursors.

In some embodiments, the kit comprises four compartments collectively comprising the ingredients i) to iv) as defined above, wherein at least one of the ingredients is comprised by an aqueous composition in one of the compartments.

In some embodiments, the device comprises four compartments: a first compartment comprising a cosmetic composition comprising i) as defined above, a second compartment comprising ii) as defined above, a third compartment comprising iii) as defined above and a fourth compartment comprising iv) as defined above.

In some embodiments, the device comprises three compartments:

(a) a first compartment comprising a composition comprising:

i) at least one entity chosen from compounds chosen from synthetic or natural compounds of formulae (I) and (II), their mesomeric forms, their stereoisomers, their addition salts with an acid or base that is cosmetically acceptable, and their hydrates; and (b) a second compartment comprising a composition comprising:

ii) at least one metal salt;

iii) hydrogen peroxide or at least one system which generates hydrogen peroxide; and (c) a third compartment comprising iv) at least one (bi)carbonate or at least one system which generates (bi)carbonate.

In such embodiments, at least one of the three compositions can be aqueous, and ingredient i) can be in the powder form.

It is also possible to have a kit comprising three compartments, the first a) comprising a composition comprising i) and ii) as defined above, the second b) comprising a composition comprising iii) as defined above and the third c) comprising a composition comprising iv) as defined above. In this other kit, at least one of the compositions is aqueous.

In some embodiments, the kit comprises two compartments, for example, a first compartment comprising a composition comprising i), ii) and iii) as defined above and a second compartment comprising iv) as defined above.

The kits comprising two compartments also include kits which comprise, in a first compartment, a composition comprising i), ii) and iv) as defined above and, in a second compartment, a composition comprising ingredient iii) as defined above.

In the alternative forms of the kit comprising two compartments, the first composition present in the first compartment comprising either i), ii) and iii) or i), ii) and iv) can be in the powder form.

In some embodiments, the device according to the disclosure furthermore comprises an additional composition (c) comprising at least one treating agent.

The compositions of the device according to the disclosure can be packaged in separate compartments optionally accompanied by appropriate applicators which can be identical or different, such as brushes, including fine brushes, or sponges.

The device mentioned above can also be equipped with a device that facilitates delivery of the desired mixture to the hair, for example such as the devices described in patent FR 2 586 913.

By way of non-limiting illustration, concrete examples of certain embodiments of the present disclosure are given below. The examples that follow serve to illustrate the invention without, however, being limiting in nature.

I) DYEING EXAMPLES

The following compositions were prepared:

| Composition A | A1 | A2 | A3 |
|---|---|---|---|
| Hematoxylin | 5 g | — | — |
| Logwood extract | — | 5 g | — |
| Brazilwood extract | — | — | 5 g |
| Hexylene glycol | 5 g | 5 g | 5 g |
| Sodium lauryl ether sulfate (70% as AM in water) | 3.75 g | 3.75 g | 3.75 g |
| Manganese chloride tetrahydrate (i.e. 0.01% by weight of $Mn^{2+}$ metal equivalent) | 0.036 g | — | — |
| Manganese gluconate (i.e. 0.01% by weight of $Mn^{2+}$ metal equivalent) | — | 0.081 g | — |
| Manganese pyrrolidone carboxylate (i.e. 0.01% by weight of $Mn^{2+}$ metal equivalent) | — | — | 0.062 g |
| Hydrogen peroxide | 1.2 g | 1.2 g | — |
| Polyvinylpyrrolidone/ $H_2O_2$ (i.e. 1.2% by weight of hydrogen peroxide equivalent) | — | — | 6 g |
| Citric acid or sodium hydroxide | q.s. for pH 5 | q.s. for pH 5 | q.s. for pH 5 |
| Demineralized water | q.s. for 100 g | q.s. for 100 g | q.s. for 100 g |

The composition A was applied to locks of dry natural hair comprising 90% white hairs and to dry permed hair comprising 90% white hairs with a bath ratio of 5 g of formulation per 1 g of hair. The treated hair was subsequently left to develop at a temperature of 50° C. for 30 minutes.

At the end, the hair impregnated with the first composition was wiped using an absorbent paper towel in order to remove the excess formulation.

| Composition B | b1 |
|---|---|
| Sodium bicarbonate NaHCO$_3$ | 2.6 g |
| Carbomer | 1 g |
| Monoethanolamine | q.s. for pH 9 |
| Demineralized water | q.s. for 100 g |

The composition B was subsequently applied to the hair with a bath ratio of 4 g per 1 g of lock; the development time was 10 minutes at ambient temperature. After a few minutes, a very intense coloring appeared. The hair was subsequently rinsed with water, washed with a conventional shampoo and dried under a hood.

Colorimetric Results:

The coloring of the hair was evaluated visually and read on a Minolta spectrocolorimeter (CM3600d, illuminant D65, angle 10°, SCI values) for the L*, a*, b* colorimetric measurements.

In this L*, a*, b* system, L* represents the intensity of the color, a* indicates the green/red color axis and b* indicates the blue/yellow color axis. The lower the value of L, the darker or more intense the color. The higher the value of a*, the redder the shade; the higher the value of b*, the yellower the shade.

The variation in coloring between the colored locks of natural/permed white hair which is untreated (control) and after treatment are defined by ΔE* according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural/permed hair comprising 90% white hairs and $L_o^*$, $a_o^*$ and $b_o^*$ represent the values measured for the untreated natural/permed hair comprising 90% white hairs.

The greater the value of ΔE, the greater the difference in color between the control locks and the dyed locks.

The coloring of the hair was evaluated visually and read on a Minolta spectrocolorimeter (CM3600d, illuminant D65, angle 10°, SCI values) for the L*, a*, b* colorimetric measurements.

| | Control (untreated hair) | Examples (on natural hair comprising 90% of white hairs) | | |
|---|---|---|---|---|
| | | 1 | 2 | 3 |
| Composition (Ai) Stage 1 | — | A1 | A2 | A3 |
| Composition (Bi) Stage 2 | — | B1 | B1 | B1 |
| Shades on hair | — | intense deep purple | intense deep purple | pink-red |
| L* | 55.6 | 20.34 | 23.1 | 35.4 |
| a* | 0.63 | 4.75 | 6.58 | 17.12 |
| b* | 14.36 | 0.9 | 0.23 | 10.08 |
| ΔE* | — | 37.97 | 35.94 | 26.42 |
| ΔL* | — | −35.26 | −32.51 | −20.2 |
| Δa* | — | 4.13 | 5.95 | 16.49 |
| Δb* | — | −13.46 | −14.12 | −4.28 |

| | Control (untreated hair) | Examples (on permed natural hair comprising 90% of white hairs) | | |
|---|---|---|---|---|
| | | 4 | 5 | 6 |
| Composition (Ai) Stage 1 | — | A1 | A2 | A3 |
| Composition (Bi) Stage 2 | — | B1 | B1 | B1 |
| Shades on hair | — | very intense deep purple | very intense deep purple | intense pink-red |
| L* | 55.19 | 18.58 | 18.69 | 27.78 |
| a* | 0.7 | 5.31 | 2.57 | 21.37 |
| b* | 13.32 | 1.76 | −0.11 | 9.43 |
| ΔE* | — | 38.67 | 38.94 | 34.56 |
| ΔL* | — | −36.61 | −36.51 | −27.42 |
| Δa* | — | 4.61 | 1.86 | 20.67 |
| Δb* | — | −11.56 | −13.43 | −3.89 |

It is apparent from the above tables that the locks of natural or permed white hair treated with the composition according to the disclosure made it possible to dye in a very chromatic and intense way, both natural and permed keratinous fibers.

II) COMPARATIVE ASSAYS

| | Composition A' | |
|---|---|---|
| | A'1 Disclosure | A'2 Comparative |
| Hematoxylin | (1.38.10$^{-3}$ mole) | — |
| Catechin | — | (1.38.10$^{-3}$ mole) |
| Hexylene glycol | 5 g | 5 g |
| Sodium lauryl ether sulfate (70% as AM in water) | 3.75 g | 3.75 g |
| Manganese chloride tetrahydrate (i.e. 0.01% by weight of Mn$^{2+}$ metal equivalent) | 0.036 g | 0.036 g |
| Hydrogen peroxide | 1.2 g | 1.2 g |
| Citric acid or sodium hydroxide | qsp pH 5 | qsp pH 5 |
| Demineralized water | qsp 100 g | qsp 100 g |

The composition A' was applied to locks of dry natural hair comprising 90% white hairs and of dry permed hair comprising 90% white hairs with a bath ratio of 5 g of formulation per 1 g of hair. The treated hair was subsequently left to develop at a temperature of 50° C. for 30 minutes.

At the end, the hair impregnated with the first composition was wiped using an absorbent paper towel in order to remove the excess formulation.

| Composition B | B'1 |
|---|---|
| Sodium bicarbonate NaHCO$_3$ | 2.6 g |
| Carbomer | 1 g |
| Monoethanolamine | q.s. for pH 9 |
| Demineralized water | q.s. for 100 g |

The composition B' was subsequently applied to the hair with a bath ratio of 4 g per 1 g of lock; the development time was 10 minutes at ambient temperature. After a few minutes, a very intense coloring appeared.

The hair was subsequently rinsed with water, washed with a conventional shampoo and dried under a hood.

Colorimetric Results

The coloring of the hair was evaluated visually and read on a Minolta spectrocolorimeter (CM3600d, illuminant D65, angle 10°, SCI values) for the L*, a*, b* colorimetric measurements.

Chromaticity: C*

Chromaticity in the CIE L*, a*, b* colorimetric system was calculated according to the following equation:

$$C^* = \sqrt{a^{*2} + b^{*2}}$$

The greater the value of C*, the greater the chromaticity is.

|  | Examples (on natural hair comprising 90% of white hairs) | |
|---|---|---|
|  | 7 | 8 |
| Composition (A'i) Stage 1 | A'1 | A'2 |
| Composition (B'i) Stage 2 | B'1 | B'1 |
| Shades on hair | intense deep purple | intense copper |
| Chromaticity (C*) | 32.50 | 11.36 |

|  | Examples (on permed natural hair comprising 90% of white hairs) | |
|---|---|---|
|  | 7 | 8 |
| Composition (A'i) Stage 1 | A'1 | A'2 |
| Composition (B'i) Stage 2 | B'1 | B'1 |
| Shades on hair | intense deep purple | intense copper |
| Chromaticity (C*) | 28.10 | 11.98 |

It was apparent from the above tables that the locks of natural or permed white hair treated with the composition according to the disclosure made it possible to dye in a significantly more chromatic way than the comparative composition (see A'1+B'1 example 7 vs. A'2+B'1 example 8) for both natural and permed keratinous fibers.

What is claimed is:

1. A method for dyeing keratinous fibers, comprising treating said fibers with:
    i) at least one entity chosen from compound chosen from synthetic or natural compounds of formulae (I) and (II), their mesomeric forms, their stereoisomers, their addition salts with an acid or base that is cosmetically acceptable, and their hydrates:

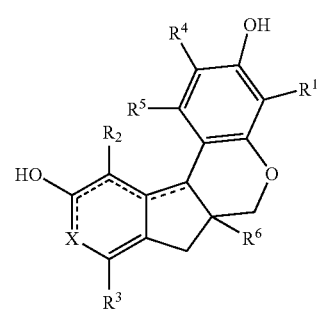

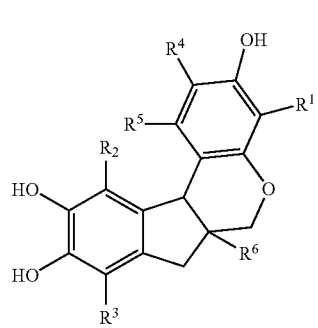

and wherein:

---- represents a single or conjugated double carbon-carbon bond;

X represents either:

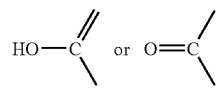

$R^1$, $R^2$, $R^3$, $R^4$, $R^5$ and $R^6$, which are identical or different, are chosen from a hydrogen atom, a hydroxy group, an optionally substituted alkyl group, optionally substituted alkoxy, and an optionally substituted acyloxy group;

ii) at least one metal salt, iii) hydrogen peroxide or at least one system which generates hydrogen peroxide, and iv) at least one (bi)carbonate.

2. The dyeing method of claim 1, wherein the at least one entity is chosen from naturally occurring compounds of formulae (I) and (II).

3. The dyeing method of claim 1, wherein the radical $R^6$ of formulae (I) and (II) represents a hydroxyl group.

4. The dyeing method of claim 1, wherein the radical $R^1$ of formulae (I) and (II) represents a hydrogen atom or a hydroxyl group.

5. The dyeing method of claim 1, wherein the at least one entity is a compound chosen from hematoxylin, brazilin, hematein, brazilein their mesomeric forms, their stereoisomers, their addition salts with an acid or base that is cosmetically acceptable, and also the hydrates, with hematoxylin, brazilin, hematein, and brazilein having the structures:

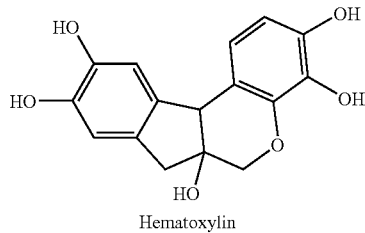
Hematoxylin

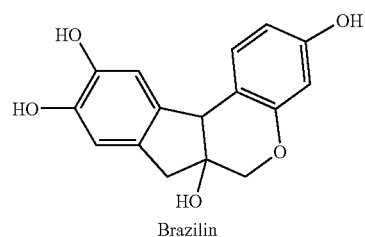
Brazilin

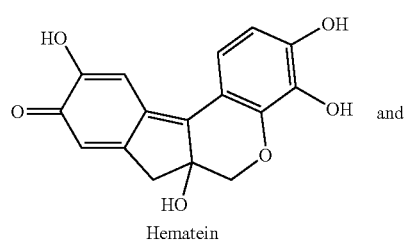
Hematein
and

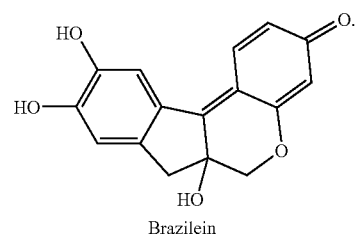
Brazilein

6. The dyeing method of claim 1, wherein the at least one entity is chosen from the compounds of formula (I).

7. The dyeing method of claim 1, wherein the at least one entity is provided in the form of a plant extract chosen from extracts of *Haematoxylon campechianum, Haematoxylon brasiletto, Caesalpinia echinata, Caesalpinia sappan, Caesalpinia spinosa* and *Caesalpina brasiliensis*.

8. The dyeing method of claim 1, wherein the at least one metal salt is chosen from Mn and Zn salts.

9. The dyeing method of claim 8, wherein the Mn and Zn salts are chosen from halides, sulfates, phosphates, nitrates, perchlorates, salts of carboxylic acids, and polymeric salts.

10. The dyeing method of claim 1, wherein the at least one metal salt is chosen from Mn and Zn oxides.

11. The dyeing method of claim 1, wherein the hydrogen peroxide or at least one system which generates hydrogen peroxide is chosen from:
   a) urea peroxide;
   b) polymeric complexes which release hydrogen peroxide;
   c) oxidases which produce hydrogen peroxide in the presence of an appropriate substrate;
   d) metal peroxides which, in water, generate hydrogen peroxide;
   e) perborates;
   f) percarbonates; and
   g) hydrogen peroxide.

12. The dyeing method of claim 1, wherein the at least one (bi)carbonate is chosen from alkali metal (bi)carbonates and alkaline earth metal (bi)carbonates.

13. The method of claim 1, wherein the method comprises a stage consisting of applying, to the keratinous fibers, a cosmetic composition comprising the at least one entity, the at least one metal salt, the hydrogen peroxide or the at least one system which generates hydrogen peroxide, and the at least one (bi)carbonate.

14. The dyeing method of claim 1, wherein the method comprises at least first and second stages, the first stage consisting of applying, to the keratinous fibers, a cosmetic composition comprising the at least one entity, the at least one metal salt, and the hydrogen peroxide or the at least one system which generates hydrogen peroxide, and the second stage consisting of applying a cosmetic composition comprising the at least one (bi)carbonate.

15. The dyeing method of claim 1, wherein the method comprises at least first and second stages, the first stage consisting of applying, to the keratinous fibers, a cosmetic composition comprising the at least one entity and the at least one metal salt, and the second stage consisting of applying a cosmetic composition comprising the hydrogen peroxide or the at least one system which generates hydrogen peroxide and the at least one (bi)carbonate.

16. The method of claim 1, further comprising, just before applying the at least one (bi)carbonate, at least one of:
   a) mechanically wiping the keratinous fibers; and
   b) drying the keratinous fibers by heating.

17. The method of claim 16, wherein the keratinous fibers are not rinsed between the mechanical wiping and applying the at least one (bi)carbonate.

18. The dyeing method of claim 1, wherein the keratinous fibers comprise pre-wetted hair.

19. The dyeing method of claim 1, wherein the keratinous fibers are treated with an aqueous composition comprising at least one of the at least one entity, the at least one metal salt, the hydrogen peroxide or the at least one system which generates hydrogen peroxide, and the at least one (bi)carbonate.

20. A cosmetic dyeing composition comprising:
   i) at least one entity chosen from compounds chosen from synthetic or natural compounds of formulae (I) and (II), their mesomeric forms, their stereoisomers, their addition salts with an acid or base that is cosmetically acceptable, and their hydrates:

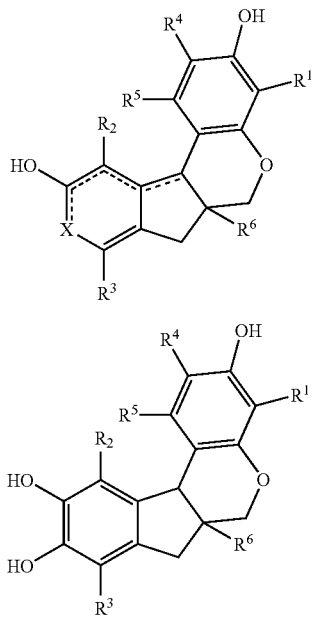

(I)

(II)

and wherein:
  ----- represents a single or conjugated double carbon-carbon bond;
  X represents either:

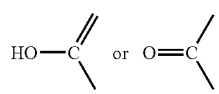

R$^1$, R$^2$, R$^3$, R$^4$, R$^5$ and R$^6$, which are identical or different, are chosen from a hydrogen atom, a hydroxy group, an optionally substituted alkyl group, optionally substituted alkoxy, and an optionally substituted acyloxy group;

ii) at least one metal salt,
iii) hydrogen peroxide or at least one system which generates hydrogen peroxide, and
iv) at least one (bi)carbonate.

21. A multicompartment device comprising from 2 to 5 compartments comprising from 2 to 5 compositions in which the ingredients
  i) at least one entity chosen from compounds chosen from synthetic or natural compounds of formulae (I) and (II), their mesomeric forms, their stereoisomers, their addition salts with an acid or base that is cosmetically acceptable, and their hydrates:

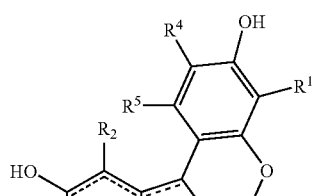

(I)

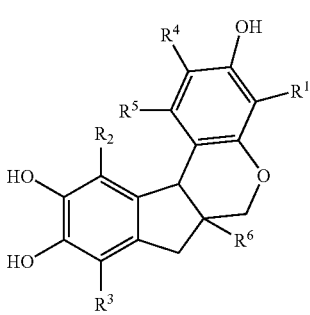

(II)

and wherein:
  ----- represents a single or conjugated double carbon-carbon bond;
  X represents either:

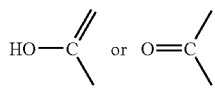

R$^1$, R$^2$, R$^3$, R$^4$, R$^5$ and R$^6$, which are identical or different, are chosen from a hydrogen atom, a hydroxy group, an optionally substituted alkyl group, optionally substituted alkoxy, and an optionally substituted acyloxy group;

ii) at least one metal salt,
iii) hydrogen peroxide or at least one system which generates hydrogen peroxide, and
iv) at least one (bi)carbonate,
and optionally water are distributed.

* * * * *

UNITED STATES PATENT AND TRADEMARK OFFICE
CERTIFICATE OF CORRECTION

PATENT NO. : 7,833,290 B2
APPLICATION NO. : 12/637220
DATED : November 16, 2010
INVENTOR(S) : Frédéric Guerin et al.

It is certified that error appears in the above-identified patent and that said Letters Patent is hereby corrected as shown below:

On the Title Page, Item (54), and Col. 1, in the Title, line 2, "HERMATOXYLIN," should read -- HEMATOXYLIN, --.

In claim 1, column 22, lines 1-15, in the structure for formula (I):

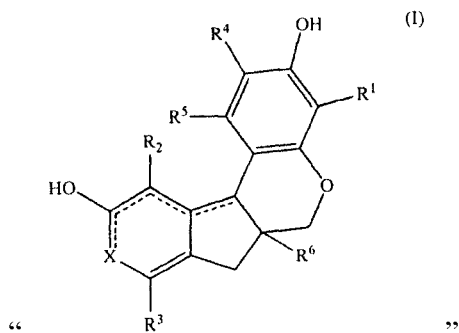

should read

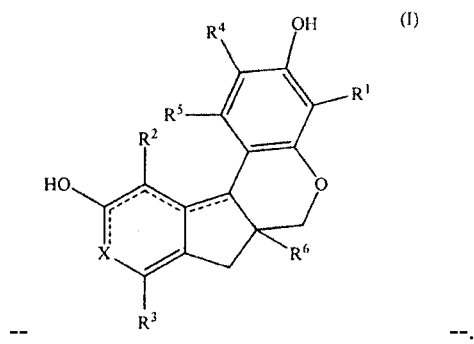

Signed and Sealed this
Eighth Day of March, 2011

David J. Kappos
*Director of the United States Patent and Trademark Office*

CERTIFICATE OF CORRECTION (continued)
U.S. Pat. No. 7,833,290 B2

In claim 1, column 22, lines 16-28, in the structure for formula (II):

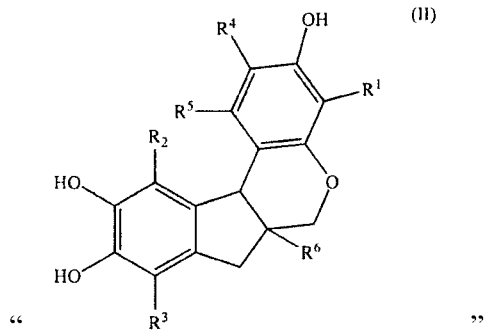

should read

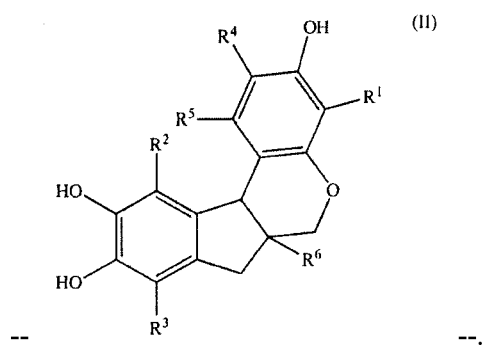

In claim 20, column 25, lines 1-14, in the structure for formula (I):

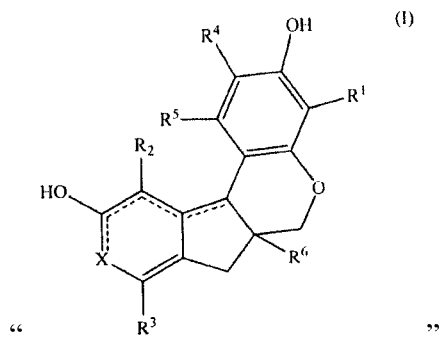

should read

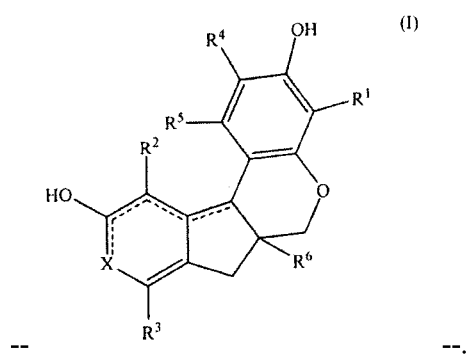

In claim 20, column 25, lines 15-26, in the structure for formula (II):

CERTIFICATE OF CORRECTION (continued)
U.S. Pat. No. 7,833,290 B2

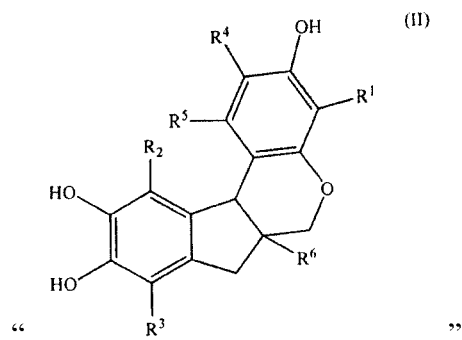

should read

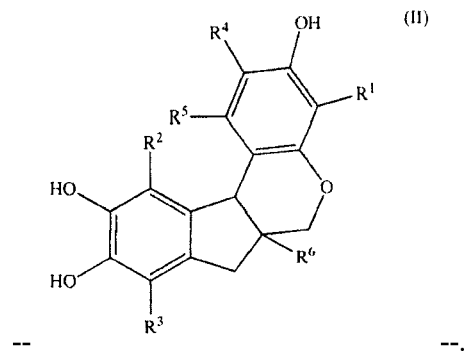

--        --.

In claim 20, column 25, line 29, "----represents" should read -- ---- represents --.

In claim 21, column 26, lines 5-17, in the structure for formula (I):

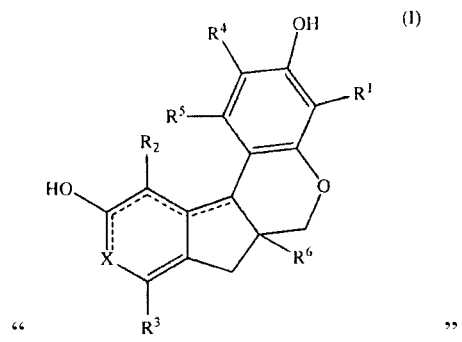

should read

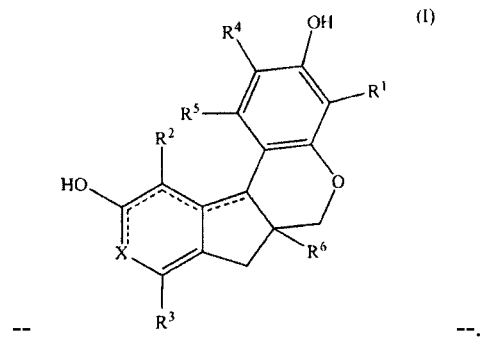

--        --.

In claim 21, column 26, lines 18-29, in the structure for formula (II):

CERTIFICATE OF CORRECTION (continued)
U.S. Pat. No. 7,833,290 B2

"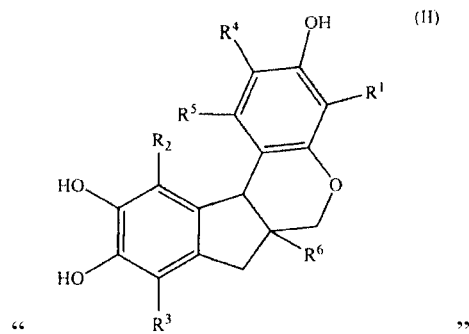"

should read

--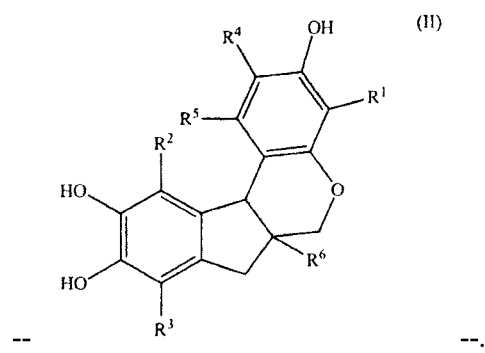--.

In claim 5, column 22, line 64, "brazilein their mesomeric" should read --brazilein, their mesomeric--.